United States Patent
Kantola et al.

(10) Patent No.: US 11,584,804 B2
(45) Date of Patent: Feb. 21, 2023

(54) METHOD FOR PRODUCING CELLULOSE CARBAMATE

(71) Applicant: ANDRITZ OY, Helsinki (FI)

(72) Inventors: Jukka Kantola, Oulu (FI); Hannu Råmark, Kotka (FI); Kyösti Valta, Tampere (FI); Kari Vanhatalo, Helsinki (FI)

(73) Assignee: ANDRITZ OY, Helsinki (FI)

( * ) Notice: Subject to any disclaimer, the term of this patent is extended or adjusted under 35 U.S.C. 154(b) by 0 days.

(21) Appl. No.: 17/057,938

(22) PCT Filed: May 21, 2019

(86) PCT No.: PCT/FI2019/050394
§ 371 (c)(1),
(2) Date: Nov. 23, 2020

(87) PCT Pub. No.: WO2019/224429
PCT Pub. Date: Nov. 28, 2019

(65) Prior Publication Data
US 2021/0206883 A1    Jul. 8, 2021

(30) Foreign Application Priority Data

May 22, 2018 (FI) ..................... 20185472

(51) Int. Cl.
| | |
|---|---|
| C08B 15/06 | (2006.01) |
| C07C 273/04 | (2006.01) |
| C08B 15/02 | (2006.01) |
| D21C 11/00 | (2006.01) |
| C05C 11/00 | (2006.01) |

(52) U.S. Cl.
CPC ............ *C08B 15/06* (2013.01); *C07C 273/04* (2013.01); *C08B 15/02* (2013.01); *D21C 11/00* (2013.01); *C05C 11/00* (2013.01)

(58) Field of Classification Search
CPC ........ C08B 15/06; C08B 15/02; C07C 273/04
See application file for complete search history.

(56) References Cited

U.S. PATENT DOCUMENTS

| | | |
|---|---|---|
| 2,134,825 A | 11/1938 | Hill et al. |
| 4,404,369 A | 9/1983 | Huttunen et al. |
| 2017/0145119 A1 | 5/2017 | Saxell et al. |

FOREIGN PATENT DOCUMENTS

| | | |
|---|---|---|
| CN | 101597336 | 12/2009 |
| DE | 44 43 547 | 5/1996 |
| EP | 2 617 708 | 7/2013 |
| FI | 62318 | 8/1982 |
| WO | 03/064476 | 8/2003 |
| WO | 03/099872 | 12/2003 |
| WO | 2011/154599 | 12/2011 |
| WO | 2011/154600 | 12/2011 |
| WO | 2011/154601 | 12/2011 |

OTHER PUBLICATIONS

International Search Report for PCT/FI2019/050394 dated Sep. 16, 2019, 4 pages.
Written Opinion of the ISA for PCT/FI2019/050394 dated Sep. 16, 2019, 5 pages.
Willberg-Keyrilainen, "Production Of Cellulose Carbamate Using Urea-Based Deep Eutectic Solvents"; Springer, (Aug. 22, 2017)(10 pages).
Koohestanian et al., "A Novel Process For CO2 Capture From The Flue Gases To Produce Urea And Ammonia" Energy vol. 144, p. 279-285 (Dec. 16, 2017)(7 pages).

*Primary Examiner* — Leigh C Maier
*Assistant Examiner* — Everett White
(74) *Attorney, Agent, or Firm* — Nixon & Vanderhye P.C.

(57) ABSTRACT

A method for controlling discharges of nitrogen compounds in the production of cellulose carbamate (CCA). Microcrystalline cellulose is produced from chemical pulp produced at a pulp mill, such that the chemical pulp is subjected to acid hydrolysis at an elevated temperature to form microcrystalline cellulose (MCC) and hydrolysate, and the MCC is reacted with urea to produce cellulose carbamate whereby ammonia is released. The microcrystalline cellulose production and the cellulose carbamate production are integrated into the pulp mill having a flue gas system such that carbon dioxide from the flue gases is reacted with released ammonia to produce urea, which is used in the carbamate production.

17 Claims, 1 Drawing Sheet

METHOD FOR PRODUCING CELLULOSE CARBAMATE

REPLATED APPLICATIONS

Figure 1:
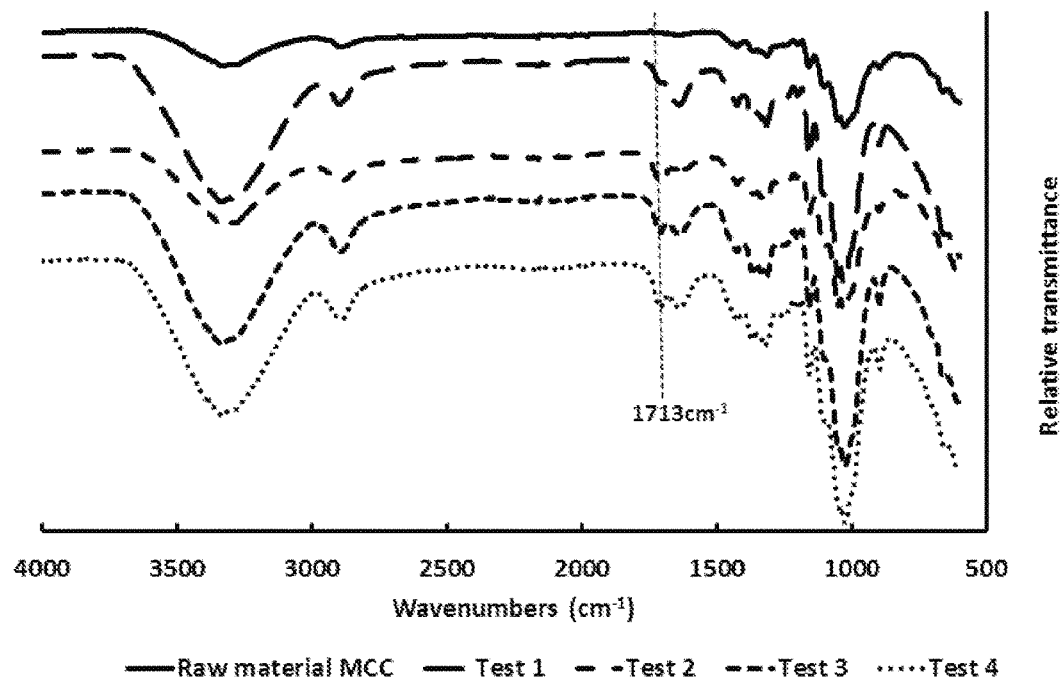

This application is the U.S. national phase of International Application PCT/FI2019/050394 filed May 21, 2019, which designated the U.S. and claims priority to Finnish Patent Application FI 20185472 filed May 22, 2018, the entire contents of each of which are incorporated by reference.

FIELD OF THE INVENTION

The present invention relates to a method for producing cellulose carbamate (CCA) which can be further processed into regenerated cellulose products, such as fibers, films, or sponges, etc. More specifically, the present invention relates to an overall process for producing CCA from microcrystalline cellulose (MCC) in a way that chemical pulp mill systems, steam, water, electricity, flue gas, wastewater treatment, and side streams of both the CCA production and the MCC production are utilized to improve the overall efficiency of each process, and discharges of nitrogen compounds in the production of CCA are controlled.

BACKGROUND OF THE INVENTION

Cellulose carbamate (CCA) is an alkali-soluble cellulose derivative invented over 80 years ago. Due to alkali solubility properties, it is a good raw material for regenerated cellulose products. Carbamated cellulose is also referred to in literature with the abbreviation "CC" and the names "urea derivative of cellulose" and "cellulose aminomethanate".

CCA is manufactured by reacting cellulose with urea or urea radical at elevated temperatures. Typically, urea is used, and it reacts with cellulose according to reaction equations (1) and (2). In the carbamation reaction, urea starts to decompose when the temperature exceeds 133° C., and the intermediate products isocyanic acid and ammonia are formed, reaction equation (1). Isocyanic acid reacts further with OH-groups of cellulose by forming a carbamate group to the cellulose backbone (2).

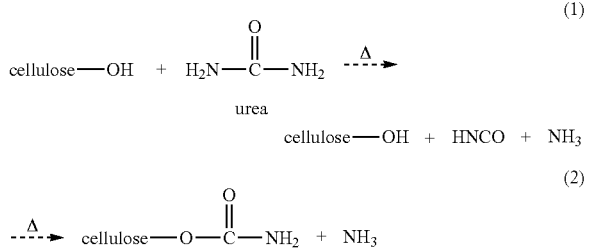

Ammonia gas, which is formed during cellulose carbamation, needs to be removed to prevent saturation of the product side of the reaction equation and to prevent the stopping of carbamation.

Due to elevated temperature, the water is evaporated and the CCA thus formed is physically in solid form. It is a stable material which can be stored and transported. These properties make it an industrially viable product.

CCA can be manufactured from all types of chemical cellulose pulps, such as kraft pulp, pre-hydrolysis kraft pulp, soda-AQ pulp, sulfite pulp, neutral sulfite pulp, acid sulfite pulp or organosolv pulp. Common features in existing carbamate techniques are starting from dissolving grade of pulp and pretreating of the pulp in order to activate it by reducing the DP (degree of polymerization). Usually the lowering of DP is done by mercerizing, by enzymes, by radiation, by catalysts and/or by mechanical means, such as milling. Activation is done to enhance chemical access inside the macro-fiber structure of cellulose and to intensify further process steps.

U.S. Pat. No. 2,134,825 discloses a process in which cellulose and urea are reacted at an elevated temperature to form an alkali-soluble product. U.S. Pat. No. 4,404,369 (FI 62318) discloses a method where an ammonia solution having urea dissolved therein is utilized and cellulose and urea are reacted at elevated temperatures to form an alkali-soluble product. WO03099872 discloses a process where cellulose is first activated with a mixture of urea and alkali, after which the liquid is pressed and the carbamation reaction is done at elevated temperatures by utilizing reactive extrusion equipment to form an alkali-soluble product. WO2003064476 discloses a CCA production method where high process consistency and processing equipment are utilized, cellulose is pre-ground before mixing it with urea and a small amount of peroxide, and the mixture is reacted at elevated temperatures to form an alkali-soluble product. DE4443547 discloses a process for the preparation of cellulose carbamate by first hydrolyzing cellulose with hydrochloride acid before the carbamation reaction, after which it is reacted with urea at elevated temperatures to form an alkali-soluble product.

Microcrystalline cellulose (MCC) is a versatile product with many industrial applications, including pharmaceuticals and food. It is also used in e.g. paints, oil drilling and cosmetic products. The Food and Agriculture Organization of the United Nations and the World Health Organization Expert Committee on Food Additives (JECFA) have issued an official definition of MCC[1].

[1] http://www.fao.org/fileadmin/user_upload/jecfa_additives/docs/monograph7/additive-280-m7.pdf MCC is a flour-form cellulose product that can be manufactured from all types of natural celluloses. It is typically manufactured by using acid hydrolysis of cellulose. WO 2011/154601 discloses a process in which fibrous cellulosic material is subjected to acid hydrolysis to produce microcrystalline cellulose. The temperature is at least 140° C. and consistency at least 8% on dry weight of cellulose. The amount of acid is low, from 0.2 to 2% on dry weight of cellulose. WO2011/154600 discloses a process in which fibrous cellulosic material is hydrolyzed with an acid at an elevated temperature to produce microcrystalline cellulose. In this document, the production is integrated to the production of a pulp mill such that at least a portion of the chemicals used in the acid hydrolysis is produced by an integrated chemical recovery process of the pulp mill.

From an economic point of view, the production costs of both CCA and MCC as a stand-alone plant are higher than when manufacturing processes are integrated to a chemical pulp mill because, in the case of integration, all the process utility systems (steam, heat, electricity, water) can be utilized. Also, waste streams can be treated in the pulp mill systems. In a stand-alone system, the main cost is the price of commercial dissolving cellulose. A stand-alone mill must handle all side streams and washing residuals and purchase all energy needed.

One reason why the carbamate cellulose technique has not achieved commercial success is the high cost due to the price of dissolving cellulose, due to investments needed for its production if done in today's viscose fiber plant, where the carbamation is also done. And finally, from fiber producers' point of view, carbamated cellulose has not been available in the market.

A chemical pulp mill is a closed process system where there exists a balance of certain elements, sodium and sulfur. Some inorganic elements, such as chlorine and potassium, enter process cycles with wood raw materials. They are removed when fly ash is taken away from the process balance. Due to the closed cycle, it is important to prevent or minimize the presence of non-process elements or totally new elements in pulp mill process cycles. Urea is needed when CCA is produced, and thus nitrogen is a new input to the process balance, and thus the amount of nitrogen needs to be minimized.

A major share of 99 million tons (62%) of the global fiber market is based on non-renewable and non-biodegradable feedstock, known as synthetic textile fibers; 24.3% on cotton, which is non-ecological; and 6.6% on viscose, which is produced by using the hazardous chemical $CS_2$ (carbon disulfide).

Viscose is the most commonly used method of producing cellulose-based regenerated fibers, and the viscose process that uses $CS_2$ accounts for over 90% of the total volume of regenerated fibers. There are other methods that are used for products, such as Lyocell, produced with ionic liquids, which are more environmentally friendly but remain niche products due to their costs and chemical recovery challenges.

Furthermore, due to the use of harmful chemicals and high costs, most of the viscose industry has been moved out of Europe. The major viscose producer in the world is China, but even there, the industry is seeking solutions for more environmentally friendly viscose.

CCA is an interesting alternative from current viscose fiber producers' point of view due to minor changes in a viscose mill when moving to a carbamate process. The biggest advantage is that the $CS_2$ chemical, which is harmful and toxic, is not used anymore, and thus the occupational health issues are much less crucial. The spinning system may be fully open, having no harmful and toxic $CS_2$ gas emissions. Another big advantage is the higher spinning production capacity with current spinning equipment due to fast precipitation speed compared to viscose coagulation speed.

MCC is an advantageous starting material for CCA products due to its high purity and high reactivity. The high reactivity comes from purity and, in this integration case, from the never-dry state of MCC before carbamation. The outcomes of these characteristics are high substitution and low urea usage in carbamation synthesis.

In view of the known processes, there is a need to develop an overall process concept, including a chemical pulp mill, MCC manufacturing and CCA manufacturing processes for producing CCA to be used as a raw material for regenerated cellulose products. There is a particular need to provide an environmentally friendly arrangement for controlling harmful emissions and one new element in the process balance of a chemical pulp mill environment, nitrogen.

DESCRIPTION OF INVENTION

The CCA plant that produces CCA by reacting MCC with urea at an elevated temperature can be a process department at a chemical pulp mill. The MCC plant that produces MCC by acid hydrolysis at elevated pressure and temperature to be used in the CCA plant can also be a process department at a chemical pulp mill. This way, both MCC and CCA plants are integrated to a chemical pulp mill.

The CCA plant, which produces CCA by reacting MCC with urea at an elevated temperature, can work with any known method which produces cellulose carbamate, but it is advantageous to use a method, which does not use organic solvents or other chemicals foreign to the chemical pulp mill environment. CCA production methods that only use urea, or urea and sodium hydroxide and/or peroxide are the most suitable, because all the chemical residues or by-products can be utilized in the chemical pulp mill.

A chemical pulp mill provides a CCA plant with process utilities, such as steam, electricity, and water, which are needed to manufacture cellulose carbamate. An MCC plant, which is integrated to a chemical pulp mill as described in publication WO2011/154600, provides MCC raw material to a CCA plant.

The CCA plant can create waste streams from:
CCA process carbamation reaction (ammonia)
CCA process washing if washing of the product is needed (unreacted urea and by-products of carbamation)

The present invention provides a method for controlling discharges of nitrogen compounds in the production of cellulose carbamate (CCA), in which method microcrystalline cellulose is produced from chemical pulp produced at a pulp mill, such that the chemical pulp is subjected to acid hydrolysis at an elevated temperature to form microcrystalline cellulose (MCC) and hydrolysate, and the MCC is reacted with urea to produce cellulose carbamate whereby ammonia is released. The microcrystalline cellulose production and the cellulose carbamate production are integrated to the pulp mill having a flue gas system such that carbon dioxide from the flue gases is reacted with released ammonia to produce urea, which is used in the carbamate production.

Ammonia gas formed in the cellulose carbamation reaction is converted back to urea, to be used again in carbamation to minimize the CCA process chemical input, by using $CO_2$, equations (5) and (6). A $CO_2$ stream can be taken from the chemical pulp mill flue-gas system, especially from the lime kiln, and led to a CCA plant carbamation reactor, or to a separate process where urea is manufactured and reused in the CCA process.

$$2NH_3 + CO_2 \rightleftharpoons NH_2COONH_4 \qquad (5)$$

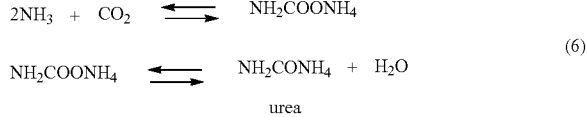

$$NH_2COONH_4 \rightleftharpoons \underset{\text{urea}}{NH_2CONH_4} + H_2O \qquad (6)$$

Urea is produced by the reaction between ammonia and carbon dioxide ($CO_2$). This is a two-step process, where the ammonia and carbon dioxide react to form ammonium carbamate, which is then dehydrated to urea. In the urea production process, ammonia and $CO_2$ are introduced in gaseous form. Both components are liquefied in a high-pressure condenser and led to a high-pressure reactor, where ammonium carbamate is formed at an elevated temperature, e.g. 180-190° C., reaction equation (5). This reaction is fast and exothermic.

An advantageous source of carbon dioxide is flue gases from a lime kiln, in which lime mud ($CaCO_3$) is burnt to lime (CaO). The partial pressure of $CO_2$ of lime kiln flue gases is higher than that of the flue gases of boilers, such as recovery boilers and power boilers, at the pulp mill, because the lime kiln flue gas includes $CO_2$ from the combustion of fuel and also $CO_2$ from the calcination reaction.

The nitrogen balance can be further controlled by using additional methods, if needed. Waste streams containing nitrogen compounds, such as unreacted urea, ammonia formed in carbamation reaction, thiourea or other by-products from the carbamation reaction, can be led fully or partly to a chemical pulp mill wastewater treatment plant, where they act as nutrient source for micro-organisms, or to an anaerobic digestion system where biogas is produced. Another option is to lead nitrogen-containing waste streams fully or partly to an evaporation plant to produce dry fertilizers. Especially in the case of washing filtrate from CCA, washing is advantageously led to an MCC process final washing stage, from which washed MCC goes to a CCA stage. With this process set-up, the amount of urea input to the CCA process can be minimized by utilizing unreacted residues.

Alkaline waste streams from the CCA plant, such as wastewater or ammonia gas, can be processed to the MCC plant and used there to neutralize
- acidic hydrolysate from the MCC reactor,
- acidic washing filtrates from washers,
- acidic condensates from the condensation system, or
- other acidic process streams.

These neutralized waste streams containing nitrogen can be further led to a chemical pulp mill wastewater treatment plant, where they act as a nutrient source for micro-organisms, or to anaerobic digestion to produce biogas. The same acidic streams from the MCC plant can also be led to the CCA plant, where the same neutralization and processing is done.

Ammonia gas formed (reaction equation (1)) in a cellulose carbamation reaction can be utilized in the pulp mill flue-gas systems to minimize NOx emission, reaction equation (3) and (4). Ammonia can be in gaseous form or in dissolved solution form when utilized.

$$4NO+4NH_3+O_2 \rightarrow N_2+6H_2O \qquad (3)$$

$$6NO_2+8NH_3 \rightarrow 7N_2+12H_2O \qquad (4)$$

Carbon dioxide emissions are believed to be a major contributor to global warming. Consequently, it is advantageous to capture $CO_2$ from flue gases of the pulp mill and utilize it as feedstock for urea.

The chemical pulp mill produces bleached fibrous cellulosic material to the MCC plant where MCC is produced. The fibrous cellulosic material may be derived from wood plant material, such as softwoods or hardwoods. A fibrous cellulosic chemical pulp can be kraft pulp, pre-hydrolysis kraft pulp, soda-AQ pulp, sulfite pulp, neutral sulfite pulp, acid sulfite pulp or organosolv pulp. It is also possible to use fibrous cellulosic material obtained from non-wood lignocellulosic plant materials such as cotton, grass, bagasse, straws of grain crops, flax, hemp, sisal, abaca or bamboo.

Example of CCA Production

The MCC manufactured from chemical pulp according to the method disclosed in WO 2011/154600 and WO 2011/154601 was carbamated according to the method disclosed in WO2003064476 to different nitrogen content levels (0.6%-1.3%) by using various urea concentrations.

In summary, bleached softwood Kraft pulp was hydrolyzed in a reactor with sulfuric acid ($H_2SO_4$). Hydrolysis circumstances were 1.5% acid dosage, 10% pulp consistency, 30-min reaction time and 160° C. temperature. The produced MCC's were washed three times using dilution thickening washing and finally centrifuged to a consistency of 45%. Carbamation was started by dosing urea to wet MCC having a dry material content of 45%. The urea dosages were 4-10% on dry content of MCC. Then, the material was homogenized in a screen compactor. The reaction was completed in an oven in which the retention time and temperature were 3.5 h and 135° C. Final CCA's were washed and dried. The nitrogen contents and DP's of the produced cellulose carbamates are shown in Table 1. Presence of carbamate groups, peak in wavenumber 1713 $cm^{-1}$, in different samples are shown in FTIR diagrams presented in FIG. 1.

TABLE 1

Nitrogen content and degree of polymerization of cellulose carbamates produced.

| | Nitrogen content (%) | Degree of polymerization |
|---|---|---|
| Test 1 | 0.6 | 210 |
| Test 2 | 0.9 | 210 |
| Test 3 | 1.0 | 220 |
| Test 4 | 1.3 | 215 |

The invention is described in more detail with reference to the appended drawings, in which FIG. 1 shows FTIR spectrums of produced cellulose carbamates. 1713 $cm^{-1}$ express presence of carbamate group in cellulose structure.

Figure 2:
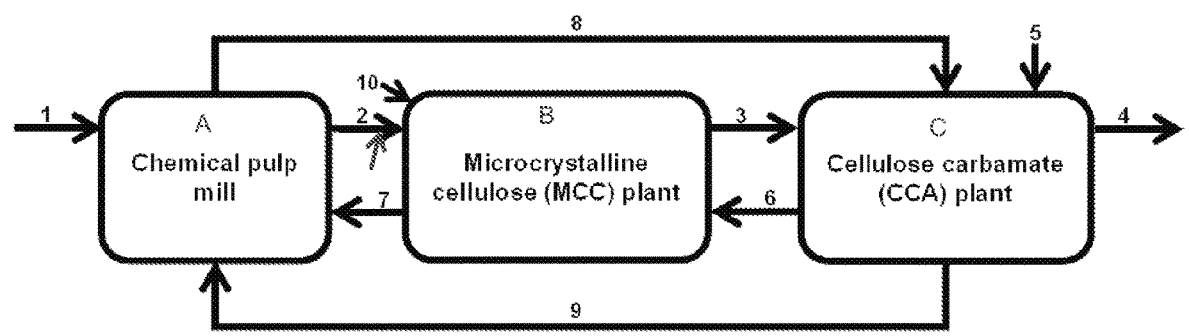

FIG. 2 is a schematic illustration of CCA production from MCC by integrating both processes to a chemical pulp mill.

The numbers and letters in FIG. 2 refer to the following streams and processing stages:
- A. Chemical pulp mill
- B. Microcrystalline cellulose (MCC) plant
- C. Cellulose carbamate (CCA) plant
- 1. Raw materials, chemical and process utilities needed to produce chemical pulp
- 2. Chemical pulp, chemicals, such as sulfuric acid, water, steam, electricity
- 3. Microcrystalline cellulose (MCC), acid stream (hydrolysate or filtrate) to neutralization
- 4. Cellulose carbamate
- 5. Urea
- 6. Alkaline wastewater/steam to neutralization or to MCC plant final washing stage
- 7. Hydrolysate, acid filtrates, condensate, clean condensate, nitrogen contain neutralized filtrate from MCC plant to a wastewater treatment plant, or to an anaerobic digestion plant to biogas production at the pulp mill
- 8. Steam, water, electricity, and $CO_2$ (urea recovery) from the pulp mill to the CCA production
- 9. Nitrogen-containing wastewater to a wastewater treatment plant or to an anaerobic digestion plant, ammonia to flue-gas systems to reduce NOx-emissions
- 10. Fresh acid, typically sulfuric acid, if needed Raw material, such as wood chips, and chemicals, typically cooking chemicals, as well as process utilities are introduced (line 1) to a chemical pulp mill A, where chemical pulp, typically kraft pulp, is produced in a way known per se.

A plant for a microcrystalline cellulose (MCC) production is integrated to the pulp mill. Chemical pulp (line 2), typically bleached kraft pulp, is led to the MCC plant, where it is hydrolyzed under acidic conditions at an elevated temperature. Acid, typically sulfuric acid, needed for the hydrolysis can be produced by using sulfur compounds recovered from gases of the pulp production. Thus, the need of fresh sulfuric acid can be decreased. Microcrystalline cellulose produced in the hydrolysis is washed and acid hydrolysate is removed from the MCC.

A plant for a cellulose carbamate (CCA) production is integrated to the MCC plant and the pulp mill. CCA is produced by reacting MCC with urea at an elevated temperature. The dry matter content of MCC is about 40-70%, and it is mixed efficiently with urea (from line 5). Then the final carbamation reaction is effected in a steam-heated mixing reactor at a temperature of 130-160° C. Ammonia is generated in the reaction. A small portion of the urea does not react, and it may be removed from the CCA product by washing. The CCA product is cooled, washed and dried, and then it is led to further processing (line 4).

Ammonia released from the carbamation process is scrubbed out of the reactor with steam and used to produce urea, which is recycled to the carbamation process. The amount of the urea supplied from an external source through line 5 can be decreased by producing urea internally. This is carried out by reacting ammonia with the carbon dioxide of flue gases from the pulp mill. An advantageous source for carbon dioxide is flue gases from a lime kiln, in which lime mud ($CaCO_3$) is burnt to lime (CaO). The urea regeneration plant is preferably part of the CCA plant.

Carbon dioxide is preferably captured from the flue gases. This can be performed by using conventional well-known methods, such as the monoethanolamine (MEA) absorption process and pressure swing adsorption (PSA) process.

The urea production is a two-step process where the ammonia and carbon dioxide react to form ammonium carbamate, which is then dehydrated to urea.

Ammonia and $CO_2$ are introduced in gaseous form. Both components are liquefied in a high-pressure condenser and led to a high-pressure reactor where ammonium carbamate is formed at an elevated temperature, e.g. 180-190° C., reaction equation (5). This reaction is fast and exothermic. The second reaction (6) is endothermic and does not go to completion. A solution comprising urea and ammonium carbamate is obtained. The ammonium carbamate present in the solution is decomposed to $CO_2$ and $NH_3$ in a recovery unit and recycled to the urea synthesis reactor. The urea process solution is led to the carbamation reactor.

Waste streams (line 9) comprising nitrogen compounds, such as unreacted urea, can be led fully or partly to a chemical pulp mill wastewater treatment plant. These waste streams can optionally or alternatively be led to an evaporation plant and produce dry fertilizers.

Alkaline waste streams (line 6) from the CCA plant, such as wastewater, may be processed to the MCC plant and used there to neutralize
  acidic hydrolysate from MCC reactor,
  acidic washing filtrates from washers,
  acidic condensates from condensation system, or
  other acidic process streams.

These neutralized waste streams containing nitrogen (line 7) can be further led to a chemical pulp mill wastewater treatment plant, where they act as a nutrient source for micro-organisms, or to anaerobic digestion to produce biogas. The same acidic streams (line 3) from the MCC plant can also be led to the CCA plant, where the same neutralization and processing is done.

The new method provides an efficient way to utilize available ammonia and carbon dioxide and thus control their emissions from the integrated CCA, MCC plant and pulp mill.

The invention claimed is:

1. A method for controlling discharges of nitrogen compounds while producing cellulose carbamate, the method comprising:
   microcrystalline cellulose is produced from chemical pulp produced at a pulp mill as the chemical pulp is subjected to acid hydrolysis to form the microcrystalline cellulose and hydrolysate, and
   reacting the microcrystalline cellulose with urea to produce cellulose carbamate during which ammonia is released,
   wherein the microcrystalline cellulose production and the cellulose carbamate production are integrated to the pulp mill having a flue gas system that handles flue gases, wherein carbon dioxide from flue gases is reacted with the released ammonia to produce the urea, which is used in the carbamate production.

2. The method according to claim 1, wherein the flue gas system is attached to a lime kiln, and the carbon dioxide is obtained from flue gases produced in the lime kiln.

3. The method according to claim 1, wherein the released ammonia is used to neutralize hydrolysate and/or acidic wastewater from the production of the microcrystalline cellulose.

4. The method according to claim 1, further comprising feeding at least a portion of nitrogen containing wastewater from the production of the cellulose carbamate to an evaporation plant which concentrates the nitrogen containing wastewater to produce dry nitrogen fertilizers.

5. The method according to claim 1, further comprising conveying nitrogen containing wastewater from the production of the cellulose carbamate to a wastewater treatment plant of the pulp mill to be used as a nutrient.

6. The method according to claim 1, wherein hydrolysate and/or acidic wastewater from the microcrystalline cellulose production is used to neutralize wastewater from the cellulose carbamate production.

7. The method according to claim 1, wherein the chemical pulp is a bleached fibrous cellulosic wood pulp.

8. The method according to claim 1, wherein the step of reacting the microcrystalline cellulose with the urea includes dosing the microcrystalline cellulose having a dry matter content in a range of 40% to 70% before being dosed with the urea, and the dosage of the urea is in a range of 4% to 10% of the dry matter content of the microcrystalline cellulose.

9. A method comprising:
   treating, in a pulp mill, chemical pulp with acid hydrolysis which yields microcrystalline cellulose and hydrolysate;
   reacting, in a microcrystalline cellulose plant integrated with the pulp mill, the microcrystalline cellulose with urea to produce cellulose carbamate and ammonia;
   extracting carbon dioxide from a flue gas flowing through a flue gas system in the pulp mill; and
   reacting the carbon dioxide with the ammonia, in a cellulose carbamate plant integrated with the microcrystalline cellulose plant and the pulp mill, to produce the urea to be reacted with the microcrystalline cellulose.

10. The method of claim 9, wherein the acid hydrolysis is at a temperature in a range of 130 to 160 degrees Celsius.

11. The method according to claim 9, wherein the flue gas system is associated with a lime kiln, and the carbon dioxide is obtained from flue gases produced in the lime kiln.

12. The method according to claim 9, wherein the released ammonia is used to neutralize hydrolysate and/or acidic wastewater from the production of the microcrystalline cellulose.

13. The method according to claim 9, further comprising feeding at least a portion of nitrogen containing wastewater from the production of the cellulose carbamate to an evaporation plant which concentrates the nitrogen containing wastewater to produce dry nitrogen fertilizers.

14. The method according to claim 9, further comprising conveying nitrogen-containing wastewater from the production of the cellulose carbamate to a wastewater treatment plant of the pulp mill to be used as nutrient.

15. The method according to claim 9, wherein hydrolysate and/or acidic wastewater from the microcrystalline cellulose production is used to neutralize wastewater from the cellulose carbamate production.

16. The method according to claim 9, wherein the chemical pulp is a bleached fibrous cellulosic wood pulp.

17. The method according to claim 9, wherein the step of reacting the microcrystalline cellulose with the urea includes dosing the microcrystalline cellulose having a dry matter content in a range of 40% to 70% before being dosed with the urea, and the dosage of the urea is in a range of 4% to 10% of the dry matter content of the microcrystalline cellulose.

* * * * *